(12) United States Patent
Guttmann et al.

(10) Patent No.: US 10,394,931 B2
(45) Date of Patent: *Aug. 27, 2019

(54) BALANCING PROVENANCE AND ACCURACY TRADEOFFS IN DATA MODELING

(71) Applicant: International Business Machines Corporation, Armonk, NY (US)

(72) Inventors: Christian Guttmann, Melbourne (AU); Xing Zhi Sun, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 586 days.

This patent is subject to a terminal disclaimer.

(21) Appl. No.: 14/994,492

(22) Filed: Jan. 13, 2016

(65) Prior Publication Data
US 2016/0124907 A1    May 5, 2016

Related U.S. Application Data

(63) Continuation of application No. 14/133,963, filed on Dec. 19, 2013, now Pat. No. 9,275,425.

(51) Int. Cl.
*G06F 17/18* (2006.01)
*G06F 17/50* (2006.01)
*G06Q 50/22* (2018.01)

(52) U.S. Cl.
CPC .......... *G06F 17/18* (2013.01); *G06F 17/5018* (2013.01); *G06Q 50/22* (2013.01)

(58) Field of Classification Search
CPC combination set(s) only.
See application file for complete search history.

(56) References Cited

U.S. PATENT DOCUMENTS

| | | | |
|---|---|---|---|
| 5,325,445 | A | 6/1994 | Herbert |
| 6,405,200 | B1 | 6/2002 | Heckerman |
| 7,675,515 | B2 | 3/2010 | Uraki |
| 7,949,186 | B2 | 5/2011 | Grauman et al. |
| 7,949,207 | B2 | 5/2011 | Nakajima |
| 8,060,342 | B2 | 11/2011 | Marvasti |
| 8,126,294 | B2 | 2/2012 | Nakajima |

(Continued)

FOREIGN PATENT DOCUMENTS

| | | |
|---|---|---|
| CN | 101110079 A | 1/2008 |
| CN | 104731843 A | 6/2015 |

OTHER PUBLICATIONS

IEEE 3D Convolutional Neural Networks for Human Action Recognition Shuiwang Ji; Wei Xu; Ming Yang; Kai Yu Published in: IEEE Transactions on Pattern Analysis and Machine Intelligence ( vol. 35 , Issue: 1 , Jan. 2013 ) pp. 221-231 IEEE.*

(Continued)

*Primary Examiner* — Michael B Holmes
(74) *Attorney, Agent, or Firm* — Reza Sarbakhsh

(57) ABSTRACT

Generating a data model may include receiving a raw data set and generating a first repository based on a first set of features of the raw data set, a second repository having a second set of features based on an aggregation of features of the first repository, and a third repository having a third set of features based on the first and second features sets. The data model may be generated based on a tradeoff between accuracy and provenance of the model.

20 Claims, 10 Drawing Sheets

(56) References Cited

U.S. PATENT DOCUMENTS

| | | | | |
|---|---|---|---|---|
| 8,275,784 | B2* | 9/2012 | Cao | G06F 17/30448 707/760 |
| 8,768,953 | B2* | 7/2014 | Pan | G06F 16/24539 707/769 |
| 8,941,656 | B2* | 1/2015 | Bak | G06T 11/206 345/428 |
| 8,947,433 | B2* | 2/2015 | Bak | G06T 11/206 345/428 |
| 8,996,581 | B2* | 3/2015 | Pan | G06F 16/283 707/797 |
| 9,043,256 | B2* | 5/2015 | Pan | G06N 5/02 706/45 |
| 9,098,550 | B2 | 8/2015 | Winkler et al. | |
| 9,210,549 | B2* | 12/2015 | Rawlinson | H04W 4/04 |
| 9,275,425 | B2* | 3/2016 | Guttmann | G06Q 50/22 |
| 9,472,098 | B2* | 10/2016 | Gao | G08G 1/09 |
| 9,495,423 | B2* | 11/2016 | Pan | G06F 16/24578 |
| 9,564,983 | B1* | 2/2017 | Cao | H04K 3/45 |
| 9,583,000 | B2* | 2/2017 | Gao | G08G 1/09 |
| 9,584,983 | B2* | 2/2017 | Rawlinson | H04W 4/04 |
| 9,942,722 | B2* | 4/2018 | Rawlinson | H04W 4/04 |
| 2015/0178622 | A1 | 6/2015 | Guttmann et al. | |

OTHER PUBLICATIONS

Journal of Machine Learning Research 3 (2003) pp. 1157-1182 An Introduction to Variable and Feature Selection Isabelle Guyon, Andre Elisseeff.*

IEEE A large-scale hierarchical multi-view RGB-D object dataset Kevin Lai; Liefeng Bo; Xiaofeng Ren; Dieter Fox pp. 1817-1824 Published in: 2011 IEEE International Conference on Robotics and Automation Date of Conference: May 9-13, 2011.*

ACM Empirical study of topic modeling in Twitter, Liangjie Hong, Brian D. Davison Proceeding, SOMA '10 Proceedings of the First Workshop on Social Media Analytics pp. 80-88 Washington D.C., District of Columbia—Jul. 25-28, 2010 pp. 1-9.*

Epshtein et al., "Feature Hierarchies for Object Classification", Proceedings of the Tenth IEEE International Conference on Computer Vision (ICCV'05), 2005.

Han et al., "Exploiting Hierarchical Domain Values in Classification Learning", SIAM International Conference on Data Mining (2004), pp. 467-471.

Kotsiantis, "Supervised Machine Learning: A Review of Classification Techniques", Informatica, vol. 31, (2007), pp. 249-268.

Patil et al., "Evaluation of Decision Tree Pruning Algorithms for Complexity and Classification Accuracy", International Journal of Computer Applications (0975-8887), vol. 11, No. 2, Dec. 2010, pp. 23-30.

Mell et al., "The NIST Definition of Cloud Computing", National Institute of Standards and Technology, Special Publication 800-145, Sep. 2011, pp. 1-7.

Pending U.S. Appl. No. 14/133,963, filed Dec. 19, 2013, entitled: "Balancing Provenance and Accuracy Tradeoffs in Data Modeling", 50 pages.

Feature overlap-based dynamic self organizing model for hierarchical text clustering Nathawitharana, N.; Matharage, S.; Alahakoon, D. Industrial and Information Systems (ICIIS), 2013 8th IEEE International Conference on Year: 2013 pp. 393-398, DOI: 10.1109/ICIInfS.2013.6732016 Referenced in: IEEE Conference Publications.

A Work-Centered Visual Analytics Model to Support Engineering Design with Interactive Visualization and Data-Mining Xin Yan; Mu Qiao; Jia Li; Simpson, T.W.; Stump, G.M.; Xiaolong Zhang System Science (HICSS), 2012 45th Hawaii International Conference on Year: 2012 pp. 1845-1854, DOI: 10.1109/HICSS.2012.87 Referenced in: IEEE Conference.

Multi-disciplinary ontological geo-analytical incident modeling Rahmes, M.; Lemieux, G.; Fox, K.; Casseus, C. Consumer Communications and Networking Conference (CCNC), 2015 12th Annual IEEE Year: 2015 pp. 77-83, DOI: 10.1109/CCNC.2015.7157950 Referenced in: IEEE Conference Publications.

Matching social network biometrics using geo-analytical behavioral modeling Rahmes, M.; Delay, J.; Fox, K.; Roe, G. Computational Intelligence and Data Mining (CIDM), 2014 IEEE Symposium on Year: 2014 pp. 422-430, DOI: 10.1109/CIDM.2014.7008699 Referenced in: IEEE Conference Publications.

* cited by examiner

BALANCING PROVENANCE AND ACCURACY TRADEOFFS IN DATA MODELING

FIELD OF THE INVENTION

The present disclosure generally relates to computerized modeling and more particularly to large scale analytics models.

BACKGROUND

Computerized data modeling may be used to facilitate a better understanding of large sets of data. Applications of data modeling techniques are broad, and may include the areas of finance, insurance, healthcare, education, and more. While gathering information is one challenge in creating an analytics model, an equally important challenge is the way in which information is presented so that it is useful.

BRIEF SUMMARY

Embodiments of the present invention provide a method, system, and computer program product for generating a computerized analytics model that receives a raw data set having a defined first set of features. A second set of features is defined based on an application of a set of domain knowledge to the first set of features, and a features hierarchy is generated based on relationships between features of the first and second sets of features. A set of features is selected from the features hierarchy, wherein as many features as possible of the second set of features are incorporated into the analytics model while maintaining a defined accuracy value. A computerized analytics model is generated based on the selected set of features.

DETAILED DESCRIPTION

Figure 1A:
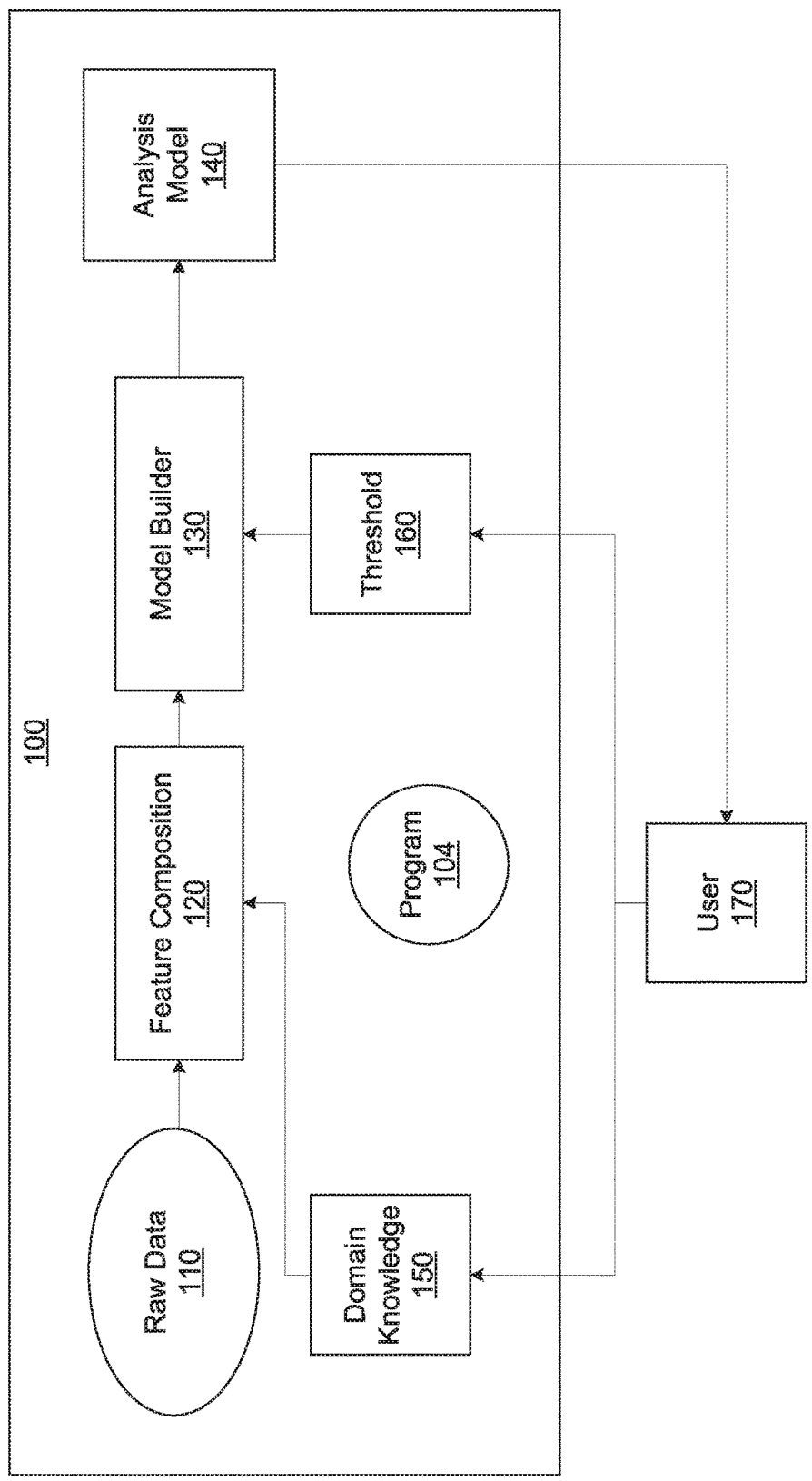
FIG. 1A is a schematic block diagram of components of a data modeling environment, according to an embodiment of the present disclosure.

Aspects of the present disclosure provide solutions for generating analytics models and data classifications that are more comprehensible compared to what is offered by existing data modeling techniques. Current modeling techniques do not provide a clear view of what features are used to shape the model and for what reason. This problem is compounded as the size of the underlying data and the complexity of the resulting data model increase. Valuable insights may go unnoticed or may even be rejected, for example, by an end user, given the complexity of the underlying features. One example is the healthcare field, wherein provenance of data is particularly important, as abstract and raw feature sets used in data mining of patient information are not easy to understand or to present even to experts in the field. Decision makers in the health care field may be reluctant to accept recommendations made by an analytics model if the model and the features it is based on are not well interpreted.

For example, a first model may predict with great accuracy, based on raw data collected corresponding to patients of various ages, that a patient over the age of 70 is 95% likely to require high cost care during each subsequent year of the patient's life. High cost care may be defined, for example, as a monetary value corresponding to the cost of medical services provided to the patient. Although the model in this example is highly accurate, it may not be apparent why the age of 70 has a role in predicting the cost of healthcare, i.e., the model may have relatively low provenance. A healthcare professional using the model in this example may be unable to identify best practices to help patients become healthier and incur a lower cost of healthcare, since the healthcare professional and the patient may have limited control over the patient's age.

On the other hand, a model generated using embodiments of the present disclosure may include more meaningful features based on collected data and information that may enable the healthcare professional and the patient to take corrective or preventative action to lower the cost of healthcare provided to the patient. For example, a second model having a relatively higher provenance level than the first model in the above example may use the same underlying data of the first model, to predict with 70% accuracy, that patients who have a blood glucose level higher than a certain value are likely to incur a high cost of healthcare. Although this second model may be less accurate than the first model in predicting whether a patient will incur high healthcare costs, the second model allows for the healthcare professional to pinpoint a factor influencing high healthcare costs that the healthcare professional can address. In this example, the healthcare professional using the second model may recommend that the patient receive treatment to reduce the patient's blood glucose levels. This is a recommendation that is not supported by the first model, even though the first model is more accurate than the second model.

Taking a classification model as an example, most existing approaches focus on building a classification model that can provide high quality performance in terms of classification accuracy. Consequently, all features in the model are often treated equally, and the selection of these features is based on their impact on classification accuracy. However, different features that may be used to generate an analytics model may carry different levels of semantics. Normally, a raw data set used for analysis in an analytics model contains basic features. The present disclosure aids in building on top of these basic features, so that new meaningful features may be developed by applying domain knowledge (e.g., healthcare domain knowledge). This may be particularly desirable where, for example, a higher provenance level is desirable given an acceptable level of classification accuracy.

Existing solutions to the problem of building a classification model based on a feature hierarchy have focused on how to maximize analytics model performance by selecting features at appropriate hierarchy levels. In order to make the model understandable, they have attempted to simplify the decision tree model by controlling the depth of the hierarchy. A better approach may be to improve the comprehensibility of the model by selecting features that are more important to the analysis desired (for example, desired by a user).

Accordingly, embodiments of the present disclosure allow for defining new features based on a data set having a set of existing features, by applying domain specific knowledge. These new features often carry more semantics applicable to the field, or domain, in which the analytics model is deployed, and can help in better understanding the model. At the same time, the model may, in some circumstances, become less accurate. However, embodiments of the present disclosure may maintain a sufficient level of desired accuracy (for example, desired by a user) so that a given model can still be useful in making predictions. Accordingly, embodiments of the present disclosure specify a threshold of model accuracy, and generate an analytics model that satisfies this minimum accuracy requirement, while maximizing the level of provenance.

Embodiments of the present disclosure may provide, without limitation, one or more of the following features and/or benefits: better classification, prioritization, and filtering of raw data and identification of models which are described using meaningful input (for example, from a user); a result generation engine that offers a better sense of what decision to take based on more meaningful information; creation of more insightful analytics outcomes based on features defined as particularly useful in a given domain; an ability to control a tradeoff between accuracy and provenance of an analytics model; and encouragement of increased use of analytics models in general.

FIG. 1A is a schematic block diagram of components of a data modeling environment 100, according to an embodiment of the present disclosure. The environment 100 may be, for example, implemented in a computer system as described in FIG. 5, below. The environment 100 may include a computer program 104 embodied within a tangible storage device. The program 104 may facilitate the environment's 100 functionality, including processing of information between its various components, as described below.

The environment 100 may further include a Raw Data 110 set that contains data pertaining to a domain, the data having varying levels of relevance and accuracy. The Raw data 110 may be stored on a tangible storage device in the environment 100. The Raw Data 110 may have one or more attributes, each of which may be considered a feature of the Raw Data 110. The domain may be defined, for example, as "healthcare". Accordingly, the Raw Data 110 may be, for example, healthcare data collected from patients during one or more visits to a healthcare facility. In this example, the Raw Data 110 may include medically relevant demographic information or other latent features such as gender and ethnicity, and may further include weight and height measurements, blood test results, etc.

Features of the Raw Data 110 may be defined and organized by a Feature Composition 120 component, and processed through a Model Builder 130 to generate an Analysis Model 140. The Analysis Model 140 may be presented to a User 170. As described above, these components may be implemented as components of the program 104, or as part of another program in the environment 100. These components are described in greater detail, below.

Although embodiments of the disclosure discuss a role of a User 170, it is not necessary that the User 170 interact with such embodiments in any instance or during any use of the respective embodiments. Furthermore, to the extent that the User 170 is involved, the User 170 may, for example, specify the User's 170 input as a preference that is applied to the modeling functionality of these embodiments automatically during each iteration.

The Feature Composition 120 component of the environment 100 may identify features of the Raw Data 110, and/or may analyze the Raw Data 110 based on a predefined set of features, to define dependencies amongst features of the Raw Data 110. Based on the defined dependencies among these features, a feature hierarchy or tree may be constructed, wherein each node of the tree represents a feature that may be linked to a parent and/or a child node(s), and each link between two nodes represents a dependency relationship. In the feature hierarchy, all basic features may be at the level of leaf nodes (i.e., it is possible that no feature depends from another feature). Examples of such feature hierarchy are shown FIG. 2, discussed below.

The feature hierarchy generated by the Feature Composition 120 component of the environment 100 may be provided to the Model Builder 130 to generate the Analysis Model 140. According to an aspect of the disclosure, in generating a model for the first time, or in modifying an existing model previously generated by the Model Builder 130, the Model Builder 130 may evaluate the corresponding model against a Threshold 160 value that defines a desired level of accuracy, such that the generated model has an accuracy level that is at least equal to the Threshold 160 value. For example, accuracy may be measured as a function of how closely the model 140 represents known information about the subject of the model 140 (for example, information of a patient whose information is collected and known in the form of the Raw Data 110) and/or how well it can predict classifications of other data objects (for example, other patients) evaluated by the model. In a related embodiment, the Threshold 160 may be a desired range of accuracy, rather than a specific value.

Applying the Threshold 160 may allow for an increase in understandability of the classification model, possibly at the expense of a lower but acceptable level of accuracy of the Analysis Model 140. The Analysis Model 140 may be more understandable and useful where it includes more high-level features of the feature hierarchy. This may be the case because high-level features often carry more semantics that reflect domain-specific knowledge. Accordingly, the Analysis Model 140 may be generated to include as many high-level features as possible without violating the defined Threshold 160 for accuracy.

The Analysis Model 140 may be iteratively modified. For example, a defined Domain Knowledge 150 (i.e., knowledge defined for the applicable domain) of the Raw Data 110 may be applied iteratively (or only once) to the Features Composition 120 to define new high-level features on top of existing low-level features. In each iteration, the modified Features Composition 120 may be processed again by the Model Builder 130 to generate a new Analysis Model 140.

In one embodiment, the Domain Knowledge 150 may be defined and/or modified by the User 170. The User 170 may be, for example, an expert in the domain that is modeled in the environment 100. In the healthcare example, the User 170 may be a healthcare expert with domain-relevant knowledge. The expert may be able to define more useful high-level features not readily definable in the Raw Data 110.

Figure 1B:
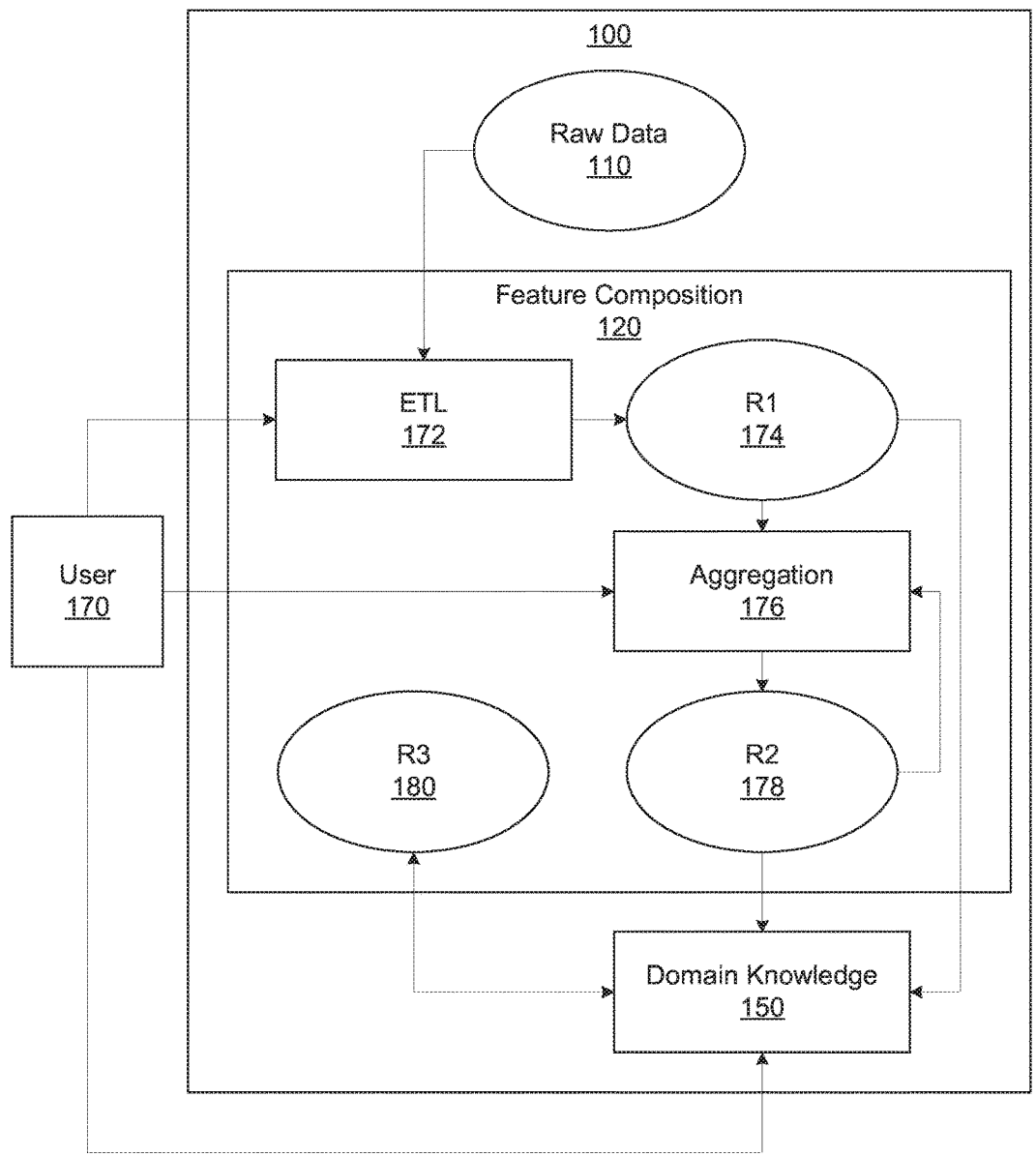
FIG. 1B is a schematic block diagram illustrating select components of the data modeling environment of FIG. 1A, according to an embodiment of the present disclosure.

FIG. 1B is a schematic block diagram illustrating select components of the data modeling environment 100 depicted in FIG. 1A, including additional components of the Features Composition 120 component, according to an embodiment of the present disclosure. An Extract, Transform, and Load (ETL) 172 component of the Feature Composition 120 component may receive the Raw Data 110 as input, and may generate a corresponding data set R1 174. The ETL 172 component may include program code that implements a corresponding process typically used in database usage and data warehousing. The ETL 172 component extracts data from the Raw Data 110 and transforms it to fit operational needs including quality levels. The ETL 172 loads the transformed data into an end target such as a database or an operational data store, data mart, or data warehouse. Exemplary ETL 172 tools include the following: Ab Initio, Anatella, Apatar, BusinessObjects Data Integrator, CloverETL, Data Moving Tool (DMT), Data Transformation Services (DTS), Feature Manipulation Engine, IBM InfoSphere DataStage, Informatica, LogiXML, MuleSoft, Oracle Warehouse Builder, Pentaho, Pervasive Software, Pipeline Pilot, SAS suites, Scripella, SnapLogic, Sprog, SQL Server INtergration Services, Sunopsis, Talend Open Studio for Data Integration, and WhereScape. All trademarks used or recited herein are the property of their respective owners.

R1 174 includes basic features identified in the Raw Data 110 by the ETL 172. In the healthcare example, these basic features may include demographics and health measurements, such as a patient's age, birthday, glucose levels, height, weight, etc. According to an exemplary embodiment, features in R1 174 data may be organized as data objects having one or more corresponding values. For example, one such data object may be a BloodGlucoseLevel data object having a corresponding numeric value.

The R1 174 data may be aggregated by an Aggregation 176 component of the Feature Composition 120 component of the environment 100 to generate a second set of data R2 178. R2 178 data may include, in the healthcare example, information gathered over time during a number of visits to a doctor, and an aggregation of such information, such as Body Mass Index (BMI) measurements, height, weight, and other information. Additional information may include the cost of providing care to patients. According to an exemplary embodiment, features in R2 178 may be, for example, a data object having one or more corresponding values. For example, one such data object may be the BloodGlucoseLevel data object having a corresponding numeric value. The numeric value may be, for example, an average of different BloodGlucoseLevel data object values found in R1 174. As a further example, an R2 178 feature may be a TotalCostOfCare data object that includes an aggregated (i.e., a running total) value of a corresponding CostOfCare data object in R1 174.

In generating R2 178 features, described above, the Aggregation 176 component of the environment 100 may transform the R1 178 features (which may be in a database system such as DB2, Oracle, an SQL server, etc.) by using a data transformation tool including, for example, an SQL tool, or a data management tool that includes a data processing component such as IBM SPSS Modeler, Mathematica, Matlab, or other ETL tools described above. These tools provide automated as well as user controllable transformation functions that allow a task to be defined and executed automatically. Other tools include functionality provided by Java, C and other programming languages to define a desired transformation of one data set to another.

In generating R2 178, the Aggregation 176 component may further define and maintain parent-child relationships between features of R1 174 and R2 178. For example, two child features in R1 174 may be used to generate a parent feature R2 178 from which both child features depend. According to one embodiment, the parent child relationships may be stored in a database table whose entries have attributes include "parent" and "child". The table can be maintained in a digital file maintained on the database and references as necessary when generating a corresponding model by other components of the environment 100.

The Domain Knowledge 150 component may define one or more high-level features based on the low-level features of R1 174 and/or R2 178, to generate a third data set R3 180. In the healthcare example, a high-level feature may be defined as a "high readmission rate" data object. Such a feature does not include data directly measured by a medical device, in the way that height, weight or blood pressure may be measured. Rather, "high readmission rate" is a feature that can be derived from underlying raw data. For example, a value for high readmission rate may be determined from the Raw Data 110 for all records related to a defined medical procedure by determining if records for patients having the procedure have additional records in the raw data 110 that indicate a subsequent stay at a hospital or other medical facility within a defined time period for a specified cause, such as post-procedure infection or other causes that can be defined, for example, as complications resulting from the procedure. For example, the values "high", "medium", and "low" may be defined per procedure, based on the number of "readmission" records for a procedure as a percentage of the number of records indicating the procedure was performed.

The definitions of high-level features in the Domain Knowledge 150 component may be applied to one or both of R1 174 and R2 178 to produce a third data set R3 180. This may be done iteratively (or once), and may involve, in some embodiments, input from the User 170. For example, the high-level features definitions in the Domain Knowledge 150 component may be applied to R1 174 features to define R3 180 features. Alternatively, or in addition thereto, they may be applied to R2 178 features to define R3 180 features. This process may be repeated through successive iterations whenever R1 174 and/or R2 178 are updated. In the healthcare example, the Domain Knowledge 150 component may be defined/configured/modified by an experienced doctor, the doctor being the User 170. However, User 170 input is not necessary. Accordingly, R3 180 may be a data repository that contains combined and aggregated features of the Raw Data 110 contained in R1 174 and R2 178, improved using domain relevant knowledge that may not be readily apparent from R1 174 and/or R2 178 for modeling. R3 180 itself may be aggregated via the Aggregation 176 component, over time. The Feature Composition 120 component may use R1 174, R2 178, and R3 180 to generate the feature hierarchy described above, with the Raw Data 110 used to define first level features R1 174, having dependent features R2 178; R1174 and R2 178 in turn may have dependent features R3 180.

R3 180 features may be generated using the same tools described above in connection with generating R1 174 and R2 178 features sets, including, for example, using the ETL 172 component, or other data processing component described above. Furthermore, generation of R3 180 may also include defining parent/child dependencies between features of R1 174 and R2 178, to which domain knowledge is applied to generate R3 180 features. This may be done in the same manner as described above in connection with generating and maintaining records of dependencies for R2 178 features.

Figure 2:
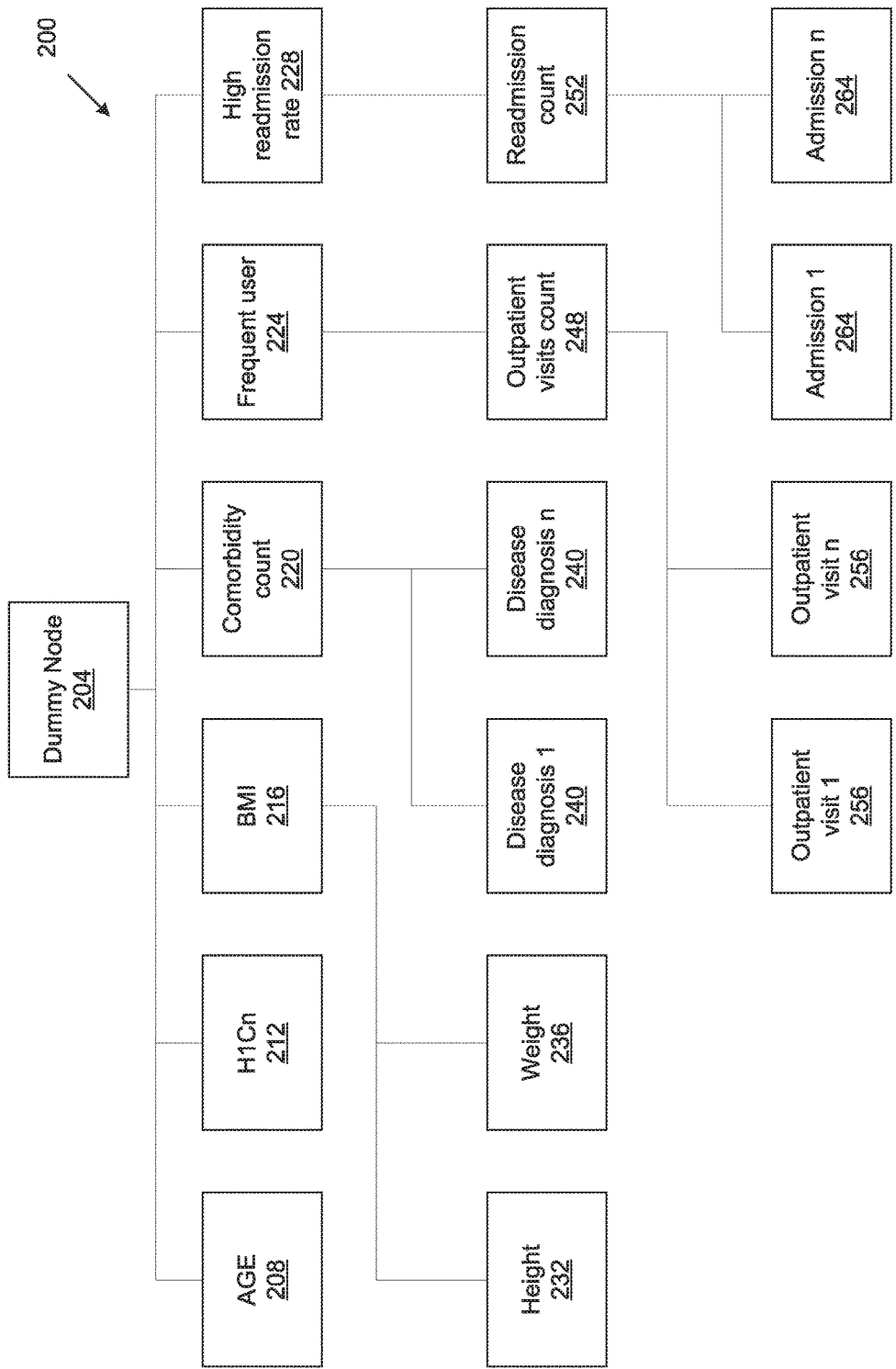
FIG. 2 illustrates an exemplary feature hierarchy, according to an embodiment of the present disclosure.

FIG. 2 illustrates an exemplary feature hierarchy 200, according to an embodiment of the present disclosure. The feature hierarchy 200 may be generated by the Feature Composition 120 component of the environment 100, as described in connection with FIGS. 1A-B, above. According to an exemplary embodiment wherein the Raw Data 110 received as input by the Feature Composition 120 includes healthcare data, the feature hierarchy 200 generated by components of the Feature Composition 120 (depicted in FIG. 1B) may include the following nodes:

- A root node 204: this may be a node defined by default as a zero-level node to serve as a root of the feature hierarchy 200 tree, from which first level features may depend.
- An age node 208—a patient's age.
- An H1Cn node 212—a patient's H1Cn reading.
- A Body Mass Index (BMI) node 216—the BMI node 216 may have the following child nodes: a height node 232 and a weight node 236.
- A comorbidity count node 220—number of diagnosed diseases a patient suffers from concurrently; the comorbidity count node 220 may have the following child nodes: diseases diagnosis nodes 240 1-n.
- A frequent user node 224—a frequent user classification may be defined as, for example, a patient who makes a number of outpatient visits greater than or equal to 4 visits in a single week. This node may have the following child nodes: an outpatient visits count node 248. The outpatient visits count node 248, in turn, may have the following child nodes: outpatient visits nodes 256 1-n.
- A high readmission rate node 228—a high readmission rate made by defined as a number of patient readmissions greater than or equal to 4 during a one-year period. This node may have the following child node: a readmission count node 252. The readmission count node 252 may, in turn, have the following child nodes: admissions node 264 1-n.

In the feature hierarchy 200, the leaf nodes (i.e., nodes that do not have a child node), may be features identified by the Feature Composition 120 component of the environment 100 as basic features R1 174. Based on information contained in these leaf nodes, other features may be defined to generate R2 178 (an aggregation of R1 174 features and R3 180 features) and R3 180 features. R3 180 features may be, for example: the frequent user node 224, the high readmission rate node 228, and the readmission count node 252, which are determined based on R1 174 and R2 180 features of the feature hierarchy 200. As can be seen from the depicted example, these R3 180 nodes/features are based on Domain Knowledge 150 features. For example, a frequent user is a defined feature that is not present in the Raw Data 110, but rather is a feature that is derived from aggregate data that is latent in the Raw Data 110. Defining a frequent user may be done dynamically by, for example, a doctor or other experienced healthcare professional (i.e. the User 170), or by an automated means, such as a computerized analytics tool and/or a database of domain specific definitions.

Figure 3A:
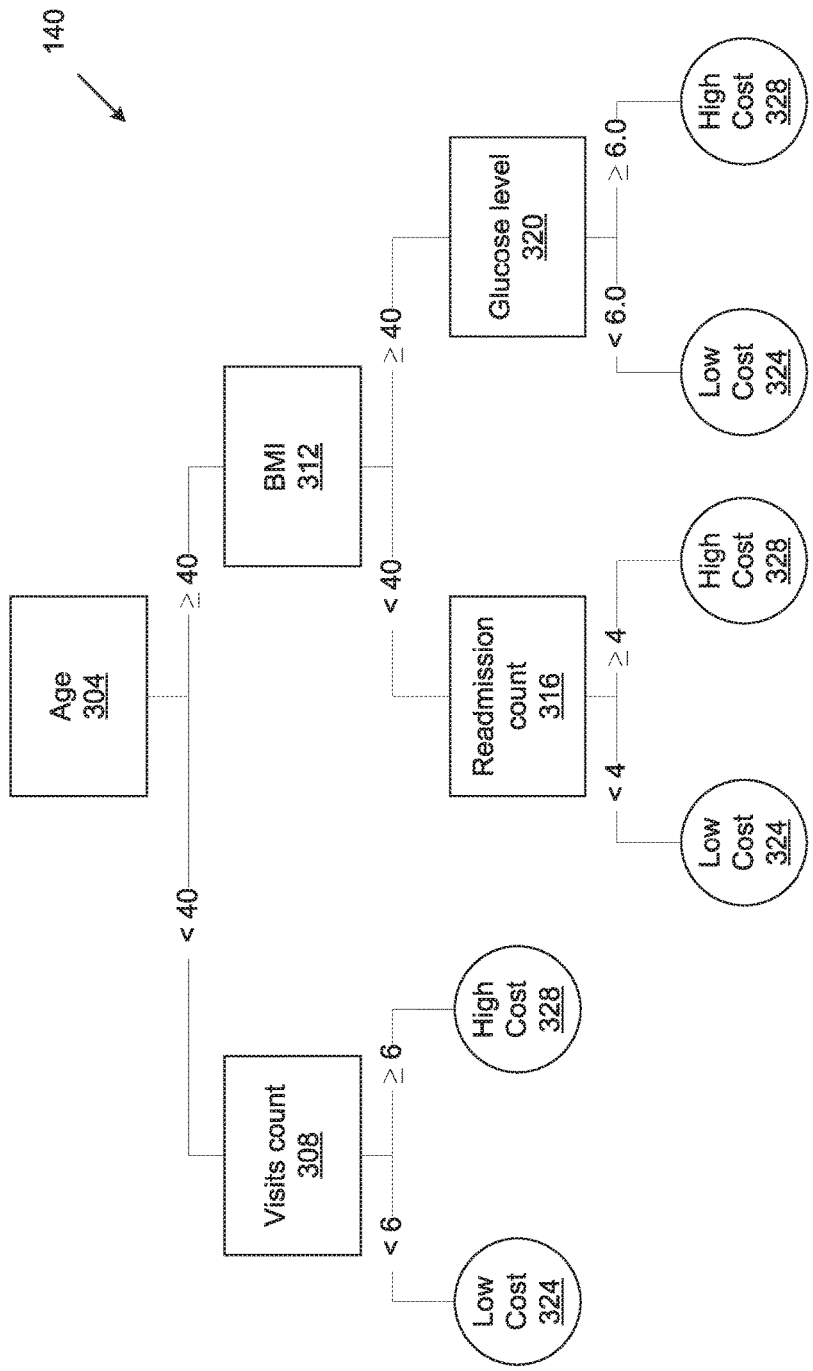
FIG. 3A is a schematic block diagram of a features hierarchy in accordance with an embodiment of the present disclosure.

FIG. 3A illustrates an exemplary decision tree model 140 (or simply, the model 140), in accordance with embodiments of the present disclosure. The decision tree model 140 is a classification model that allows for assigning a class label to a data object. Other embodiments may use a different classification model, such as a Support Vector Machine (SVM) classifier, a logistic regression model, or other classification models. These models may be in the form of a mathematical formula or model and may be applied to a feature hierarchy. The model 140 may correspond to a classification of one patient, or it may contain aggregate classifications of multiple patients.

In the present embodiment, the model 140 is based on the feature hierarchy 200 in FIG. 2. The model 140 may assign a class label to a data object as follows: a low cost label 324 or a high cost label 328. The data object may be, for example, a patient record having a set of associated data corresponding to the patient. The model 140 may include the following nodes:

- An age node 304 serving as a root node—the age node 304 has two branches: a first branch corresponding to ages younger than 40 years old, and a second branch corresponding to ages of 40 years old and above.
- A visits count node 308 serving as a child node of the root node, itself having two branches corresponding to values of fewer than six, and greater than or equal to 6. The first of these two branches has the classification low cost 324 as its child node, and the second branch has the classification high cost 328 as its child node.
- A Body Mass Index (BMI) node 312, itself having two branches and two corresponding child nodes. The branches are: less than 40, and greater than or equal to 40.
- A readmission count node 316 that is a child node of the BMI node 312 through the younger-than-40 branch. The readmission count node 316 itself has two branches of fewer than 4, and greater than or equal to 4, the first branch leading to the low cost label 324 as a child node, and the second branch leading to the high cost label 328 as a child node.
- A glucose level node 320 that is a child node of the BMI node 312 through the 40 or older branch. The glucose level node 320 itself has two branches: a first branch of less than 6.0 (i.e. a glucose level less than 6.0), and a second branch of greater than or equal to 6.0. The first branch leads to the low cost label 324 as a child node, and the second branch leads to the high cost label 328 as a child node.

As described above, two aspects of the model 140 that may be used to evaluate its usefulness may include: accuracy and provenance. Accuracy of the model 140 may be defined as a measure of how closely the model 140 represents known information about the subject of the model 140 (for example, information of a patient whose information is collected and known in the form of the Raw Data 110) and/or how well it can predict classifications of other data object (for example, other patients) evaluated by the model. Accuracy may be measured as a percentage value or as another value. Accuracy may be determined, for example, by splitting instances (e.g., data objects corresponding to patient records) having known classifications (e.g., high-cost vs. low-cost) into two sets: a training dataset and a testing dataset. The split may be, for example, 80%/20%, respectively. The training dataset may be used to build a classification model based on a modeling algorithm, and the classification model may be applied to the test dataset to test the accuracy of the model, represented as a proportion of correctly classified instances (e.g., patient records) out of the total number of instances in the test dataset. Classification of the test dataset by the model may be deemed correct where it matches known classifications for the test dataset.

Provenance may be measured by associating R1 174 features, R2 178 features, and R3 180 features a weighted value, wherein the higher level a feature is, the higher weighted value it has. Accordingly, a given model's provenance may be increased by including more high-level features in the model. One reason for this is that high-level features represent domain relevant knowledge; they represent deeper insight than offered by lower level features.

Provenance of the model 140, on the other hand, may be defined as a measure of clarity of why the model predicts a given classification. It may be based on, for example, how many high level features the model includes. For example, each feature used in the model may be assigned a weight according to the level of the features hierarchy it is selected from, whereby leaf nodes of the features hierarchy have a lowest weighted value, and parent nodes have a higher weighted value according to the number of child nodes they have. A model having a highest provenance may be one that has the highest number of high-level features.

In some circumstances, it may be the case that a higher provenance leads to lower accuracy, and vise versa. For example, this may be because a first model having a relatively higher provenance than a second model contains fewer low-level features than does the second model. The first model may have lower accuracy because, for example, high-level features are based on definitions (including, for example, definitions based on domain relevant knowledge) that are defined with a degree of subjectivity. For example, an R3 180 feature such as "high readmission rate" having a definition of "4 or more readmission rates in a one-month period" may be defined with input from a healthcare professional. The definition may be based on subjective observations of the healthcare professional about what feature/information is useful to the healthcare professional. Therefore, the information supplied to the Domain Knowledge 150 component to define high-level features such as those in R3 180 are not necessarily correct. They serve as a tool in developing a model, but the model may not be entirely accurate. Accordingly, increasing provenance may lead to a decrease in accuracy as the model relies more on features whose definitions are applied to collected data rather than features that are derived from the collected data.

In one exemplary model (not shown) similar to the model 140 depicted in FIG. 3A, the exemplary model may include only the age node 304. The exemplary model may assign the low cost label 324 to any patient (represented as a data object) younger than 40 years old, and the high cost label 328 to any patient 40 years old and above. This model may be 90% accurate. In other words, it may be that for 90% of patients evaluated using this exemplary model, a patient's age is an accurate indicator of how costly it is to provide that patient with healthcare services. However, this single node exemplary model may be vague as to why this is the case. In other words, it may not be readily apparent (i.e., there may be low provenance) why the age of 40, which is an R1 174 feature in the feature hierarchy 200, is a significant feature in determining healthcare costs. Therefore, while highly accurate, this exemplary model (not shown) may be deemed to have low provenance and may be considered relatively unhelpful.

The model 140 in FIG. 3A may include more features that the exemplary model (not shown) discussed above. The model 140 may be generated, for example, using the following record R (i.e., a data object) which may be available for a given patient P for whom a modeling is desired: {age: 52; visits count: 1; BMI: 30; readmission count: 2; glucose level: 7.0; H1Cn: 6.0; frequent user: no}. P may be evaluated against the model 140 (using R) beginning with the age node 304. Since P is over 40 years of age, P's classification is evaluated through the greater-than-or-equal-to branch of the model 140. Accordingly, P is next evaluated with respect to the BMI node 312. Since P's BMI is less than 40, P is next evaluated with respect to the readmission count node 316. Since P's readmission count is fewer than 4, P is assigned the low cost label 324. This classification may be used (for example, by a computer system used by P's health insurance provider) to determine the cost that P represents to the provider.

In the above example, the model 140 may be determined to have 90% accuracy. In other words, the model may correctly predict a high/low cost classification with 90% certainty. While highly accurate, the model 140 in this example may not have a high provenance level. In other words, it may not be apparent (for example, to P's health insurance provider) why a patient that has a record R as in P's case should be considered as low cost, even if that is in fact the case 90% of the time. The relatively low provenance may be due, in this example, to the fact that while the model 140 incorporates R1 174 and R2 178 level features of the Raw Data 110, it does not include any features from R3 180, as defined in connection with the feature hierarchy 200 (FIG. 2). Therefore, while accurate, the model may not be very useful. Accordingly, it may be desirable to generate a model that evaluates P in light of measures whose provenance is better understood.

Figure 3B:
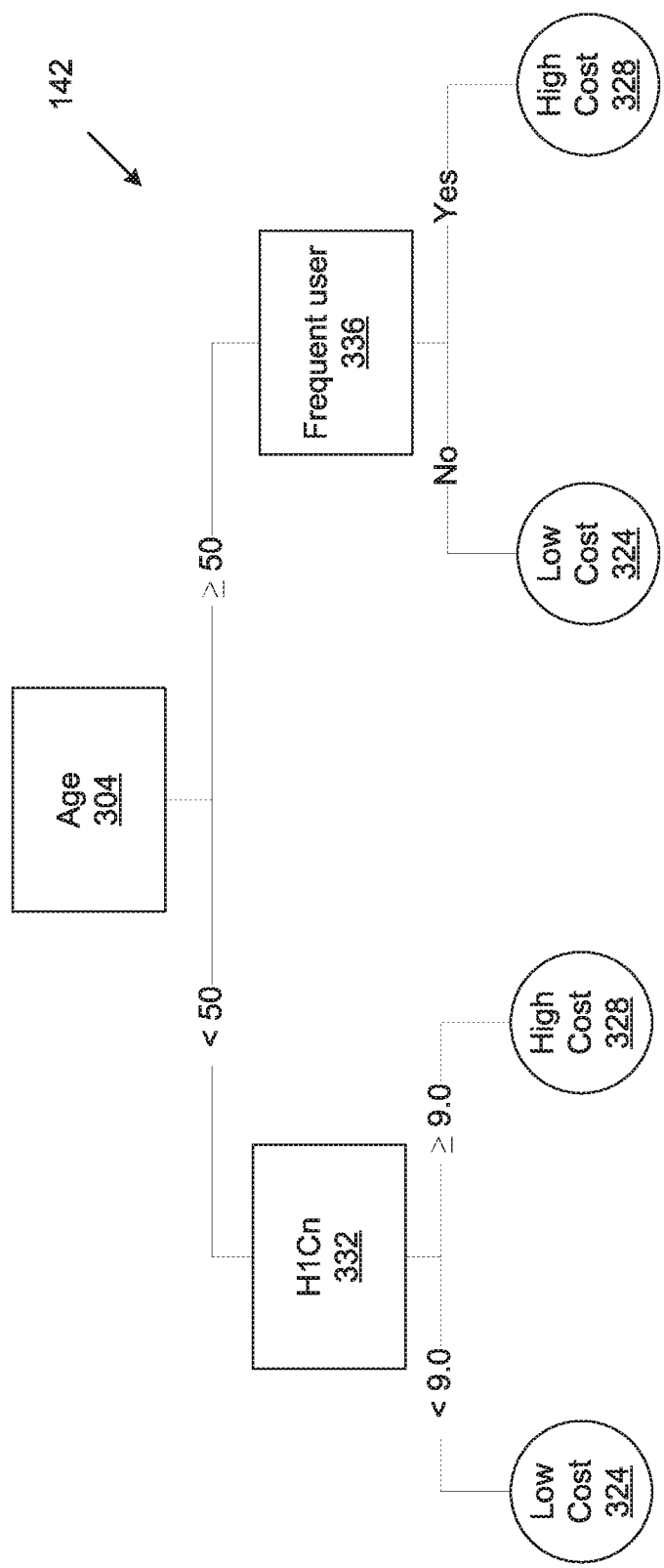
FIG. 3B is a schematic block diagram of a decision tree model in accordance with an embodiment of the present disclosure.

FIG. 3B illustrates an exemplary decision tree model 142 (or simply, the model 142), in accordance with embodiments of the present disclosure. The model 142 may be a modified model 140, or it may be an original model (i.e., it is not necessary to generate the model 142 based on the model 140). The model 142 may have a lower accuracy (e.g. 80%) compared to the model 140, but may have higher provenance. In other words, it may correctly classify patients as low cost vs. high cost for only 80% of the patients evaluated using the model (vs. the 90% accuracy of the model 140), but it may provide greater provenance in each case, as described below.

In this example, the model 142 may have the following nodes:
  The age node 304 having two branches: below 50, and equal to or greater than 50.
  An H1Cn node 332, which is a child node of the age node 304 from the less than 50 branch, itself having two branches: a less than 9.0 branch that corresponds to a low cost label 324, and a greater than or equal to branch that corresponds to a high cost label 328.
  A frequent user node 336, which is a child node of the age node 304 from the greater than or equal to 50 branch, itself having two branches: a no branch that corresponds to a low cost label 324, and a yes branch that corresponds to a high cost label 328.

The same patient P whose record R yields a low cost classification according to the model 140 in FIG. 3A may be evaluated against the model 142. P may first be evaluated relative to the age node 304. Since P is not younger than 50 years of age, P is next evaluated relative to frequent user node 336. Since P is not a frequent user (as defined in the feature hierarchy 200 in FIG. 2) P is assigned the low cost label 324. This classification may be more understandable; i.e., it may be more apparent why a patient like P is low cost. Accordingly, one conclusion that may be reached from a review of the results of the model 142 as applied to P may be: patients who are 50 years of age or older who are not frequent healthcare users represent a low cost. This is a conclusion that is not supported clearly in the model 140. Therefore, while the model 140 may predict low cost vs. high cost classifications with greater accuracy than the model 142, the model 142 may provide more insight and allow for better inferences.

Figure 4A:
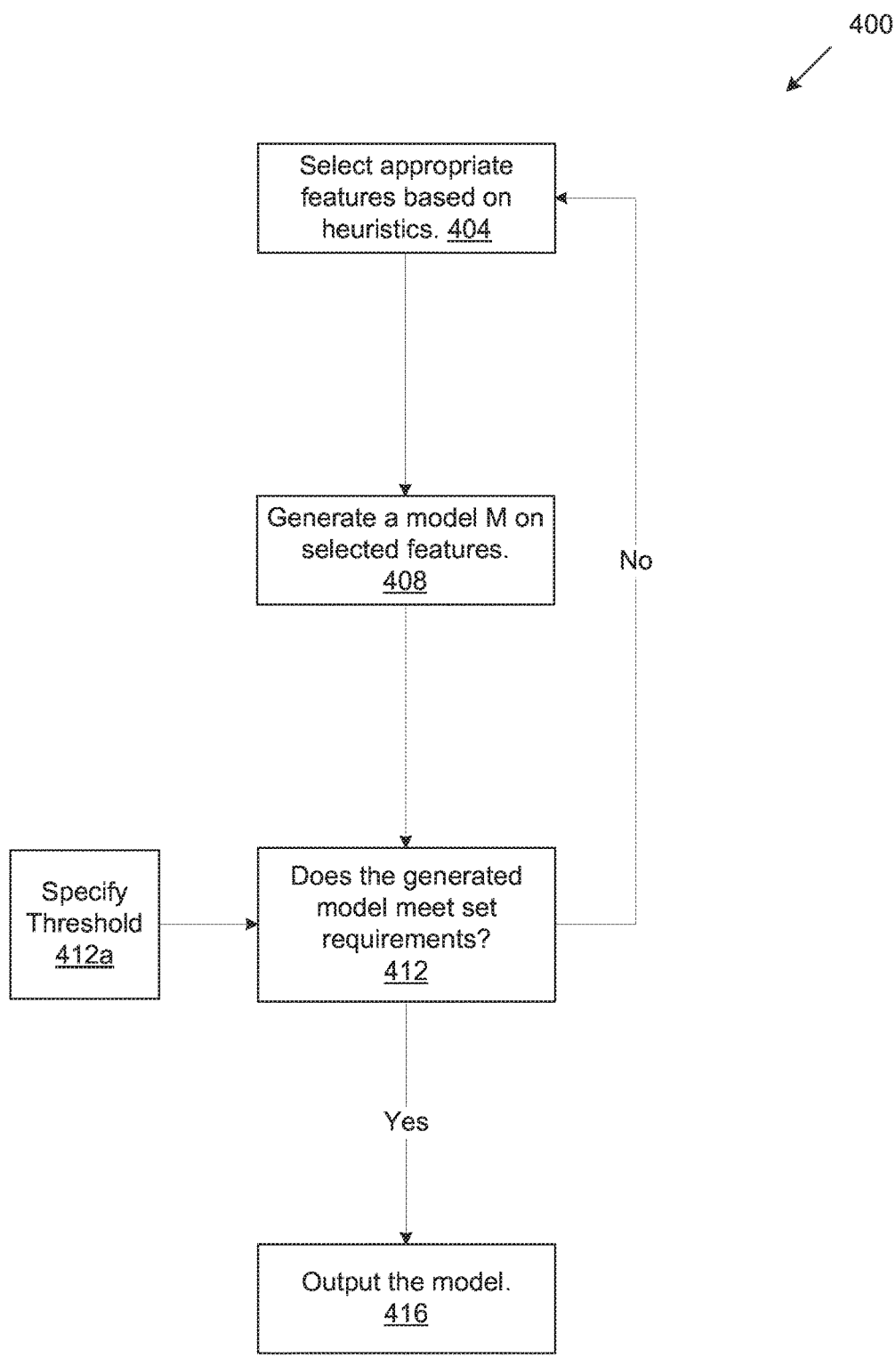
FIG. 4A is a flowchart illustrating steps of a method for generating an analytics model according to an embodiment of the present disclosure.

FIG. 4A is a flowchart illustrating steps of a method 400 according to an embodiment of the present disclosure, to generate an analytics model M, which may be, for example, the model 142 depicted in FIG. 3B. The method 400 may be implemented by, for example, the program 104 as part of the environment 100, depicted in FIG. 1. The method 400 may receive a feature hierarchy as an input. This may be the feature hierarchy 200, depicted in FIG. 2. The method 400 may generate a model M (e.g., the models 140-142 shown in FIG. 1A-B, 3A-B) that meets an accuracy Threshold 160 value (which may be configurable by the User 170) specified in step 412a, and may incorporate as many high-level features as possible given the threshold requirement.

Accordingly, the method 400 may select one or more features from the data sets R1 174, R2 178, and/or R3 180, based on a heuristics approach, at 404, and generate M based on selected features thereof in step 308. Through the heuristics approach, the method 400 analyzes a number of models that can be generated from the features hierarchy, and compares them to one another to determine which model includes a highest number of high-level features from the features hierarchy while maintaining an accuracy that meets the threshold accuracy criteria. Additional details of selecting features based on heuristics are described in more detail in connection with FIG. 4B, below. The method 400 may determine, in step 412, whether the generated M meets the accuracy requirement specified in step 412a, and whether it includes as many high-level features as possible given this threshold. Upon determining that it does, the method 400 outputs M in step 316 (for example, on a display).

Upon determining that M does not meet the requirements set by the User 170, in step 412, the method 400 may iteratively select appropriate features based on additional heuristics data in step 404. The method 400 may, at each iteration, make recommendations of features to select, including, for example, features or a combination of features not selected during an earlier iteration, such that the model generated in step 408 will be different from an earlier model deemed unacceptable or undesirable in step 412. No model may be presented if every iteration (for example, a predetermined number of iterations) results in an unsatisfactory model.

A challenge in performing the method 400 may be large numbers of candidate feature sets present in the data sets used as input. Mathematically, if the number of features in the features hierarchy is N, there are ($[2^{(N-1)}]-1$) candidate feature sets, where N is the total number of features including an empty feature (e.g., a dummy node serving as a root node of the features hierarchy). In the feature selection step 404, therefore, application of heuristics becomes useful to quickly find an appropriate set of features that may generate a desirable model. As discussed above, the heuristics approach includes generating a set of models from the same features hierarchy and determining which model in the set of generated models includes a highest number of high-level features of the features hierarchy while maintaining an accuracy level that meets the accuracy threshold requirement of the method 400. Intuitively, the heuristics may apply some rules to traverse the feature hierarchy such that the set of features that can lead to optimal or near optimal modeling may be found quickly. In each iteration, the new selected feature set may be determined based on a current feature set, a structure of the feature hierarchy, and a current model and its determined accuracy.

According to an embodiment of the disclosure, the step 404 heuristics that are used for feature selection may be defined as follows. As part of the selection process, the method 400 may first analyze a root of the feature hierarchy, supposing that there always is one root node at a hierarchy level 0. This may be, for example, a dummy node. The dummy node is the most general node of the feature hierarchy. High-level features refer to the features located in an upper level of the hierarchy. Conversely, low-level features refer to the features located in a lower level of the hierarchy. By progressively traversing the features hierarchy through successive levels, from high-levels to low-levels, features may be selected to generate one or more corresponding models, and an accuracy measure may be updated. If the accuracy requirement is met, the search may stop and lower-level and more specific features need not be searched. For example a search may be started at a level 1. If a model generated from this initial feature set (i.e., the set of features at level 1) is not accurate enough, a feature at level 1 may be replaced in the model by its child features found in level 2.

Selection of features by the method 400 in step 404 may be enhanced by evaluating the effect and/or impact of a feature in the features hierarchy on the model generated using the features hierarchy. The method 400 may use a measure indicating the feature's significance in and/or its impact on the model. For example, when evaluating a feature as part of a decision tree model, one such measure may be an information gain measure. An information gain measure is a measure of change in an entropy value of a decision tree model when one feature is used in the model to partition instances (data objects) into subsets. Entropy is a measure of discord or impurity of the output values of a set of instances. The output value may be, in the case of a classification model, a class label (e.g., high cost or low cost) for a given instance, i.e., a data object vector (e.g., a patient record). Where S is a set of instances for generating the model, and $p_i$ is the fraction of instances in S with an output value of i, entropy of S may be defined as:

$$\text{Entropy }(S) = -\Sigma_i p_i \log_2(p_i)$$

Given the above definition of entropy, information gain of a feature A may be determined as:

$$\text{Gain}(S,A) = \text{Entropy}(S) - \Sigma_{v \text{ in } Values(A)}[(|S_v|/|S|) * \text{Entropy}(S_v)]$$

where S is a set instances for generating the model, v is a value of a feature A, $S_v$ is the subset of S with A=v, and Values (A) is the set of all possible values of A.

Information gain (and its underlying entropy value(s)) is only one example of a measure that may be used in evaluating a feature's significance in and impact on a corresponding model, for example, a decision tree classification model. Other classification models may use a different measure. For example, a logistics regression model may use a p-value measure, which is an indication of a feature's statistical significance in the model.

Which model is selected by the heuristics procedures of step 404 of the method 400 may therefore be based on the features of the model having a preferred, predetermined, or specified impact on the model. For example, a feature may have a preferred impact relative to another feature where its inclusion in a corresponding model yields a lower entropy value. Such preferences may be predefined and/or specified by a user based on the particular modeling that is used and/or desired/preferred.

In this example, if the model is not accurate enough, a feature having the least significant entropy value may be the one replaced with its child features at the next level. This approach preserves general features that are believed to be important for building the model, and breaks up those features that are relatively narrower and less important to the model.

Once a feature set selected in step 404 is broken down in favor of a new set of selected features, a new feature set is created. A new model may be generated in step 408 based on the new feature set. If performance of the new model is no greater than that of the previous model M, the broken down feature set may be ignored, and the breakdown may be undone in favor of a new breakdown of another feature having the second least significant entropy value.

The feature breakdown process may continue until a resulting model is accurate enough, or if every feature in a selected feature set is a leaf node in the feature hierarchy.

Figure 4B:
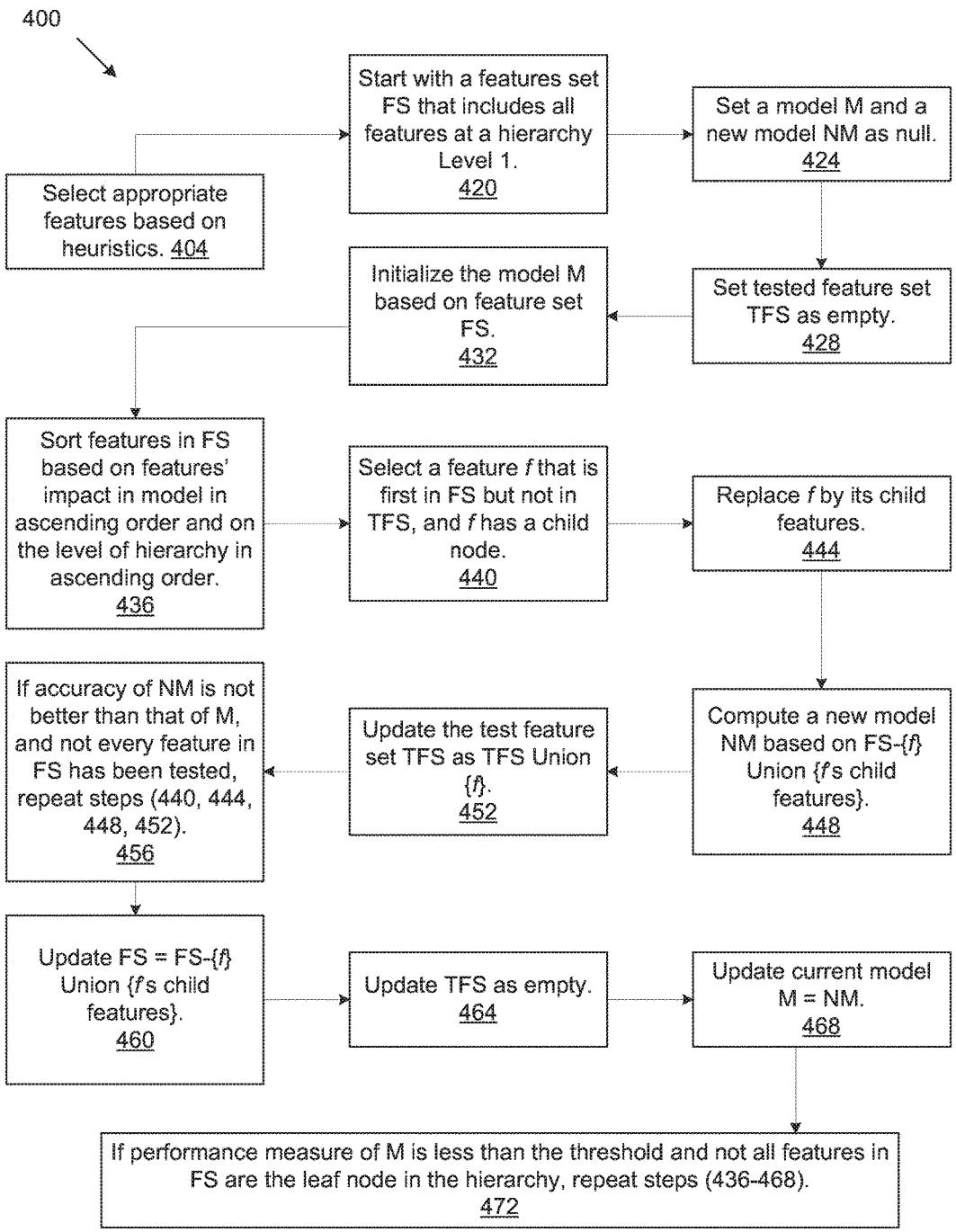
FIG. 4B is a flowchart illustrating additional steps of the method of FIG. 4A, according an embodiment of the present disclosure.

Referring now to FIG. 4B, the heuristics approach of step 404 (FIG. 4A) of the method 400, according to an exemplary embodiment of the present disclosure, includes the following steps. The method 400 may start with a feature set FS that includes all features at a hierarchy in a first level, e.g. level 1, in step 420. The method may assign a null value to a model M and a new Model NM, in step 424. The method 400 may also initialize a tested feature set TFS as empty.

The method 400 may initialize the model M based on the feature set FS, in step 432. The features of FS in model M may be sorted based on their entropy values in relation to the model M. The sorting may be in ascending order. The features may also be sorted according to their level in the features hierarchy. This sorting also may be in ascending order. Other sorting policies are possible.

The method 400 may select, in step 440, a feature f that is first in FS but not in TFS, where f has a child node in the feature hierarchy. In step 444, the f selected in step 440 may be replaced by its child features.

In step 448, the method 400 may compute a new model NM (which may have been initialized in step 324) based on: FS-{f} Union {f's child features}. The test feature set TFS may be updated as TFS Union {f}, in step 452.

Accuracy of the model NM may be evaluated in step 456 and compared to that of M. If NM's performance is no better, then steps of selecting a feature f 440, replacing it with its child features 444, computing a new model 448, and updating a test feature set 452, may be repeated and evaluated again in step 456.

Upon determining that the accuracy of NM is better than M, in step 456, the method 400 may proceed to update FS=FS-{f} Union {f's child features}, in step 460. TSF may be updated as empty in step 464, and M may be set to equal NM.

M's accuracy may again be evaluated in step 472 to determine whether it is less than the Threshold Metric 160 (see FIGS. 1A-B) and whether all features in FS are leaf nodes in the features hierarchy. If M is less than the Threshold Metric 160, and not all features in FS are leaf nodes, the method 400 may repeat steps of sorting 436, selecting 440, replacing 444, computing 448, updating 452, evaluating 456, setting 460, updating 464, and updating 468, to arrive at a new M. This new M may again be evaluated in step 472, or the method 400 may present M as described in connection with FIG. 4A, or the method 400 may terminate.

With continued reference to FIGS. 4A-B, as described, the method 400 facilitates, in part, setting a threshold for accuracy, and evaluates the model M in relation to that threshold. Other constraints on provenance may be used; for example, a requirement that at least 3 features from R3 180 (FIGS. 1B, 2), or a specific feature, must be in the model. The method 400 may, therefore, generate M to satisfy the accuracy requirement and to satisfy provenance requirements. The provenance requirement may be based on the User's 170 (FIGS. 1A-B) input.

Figure 5:
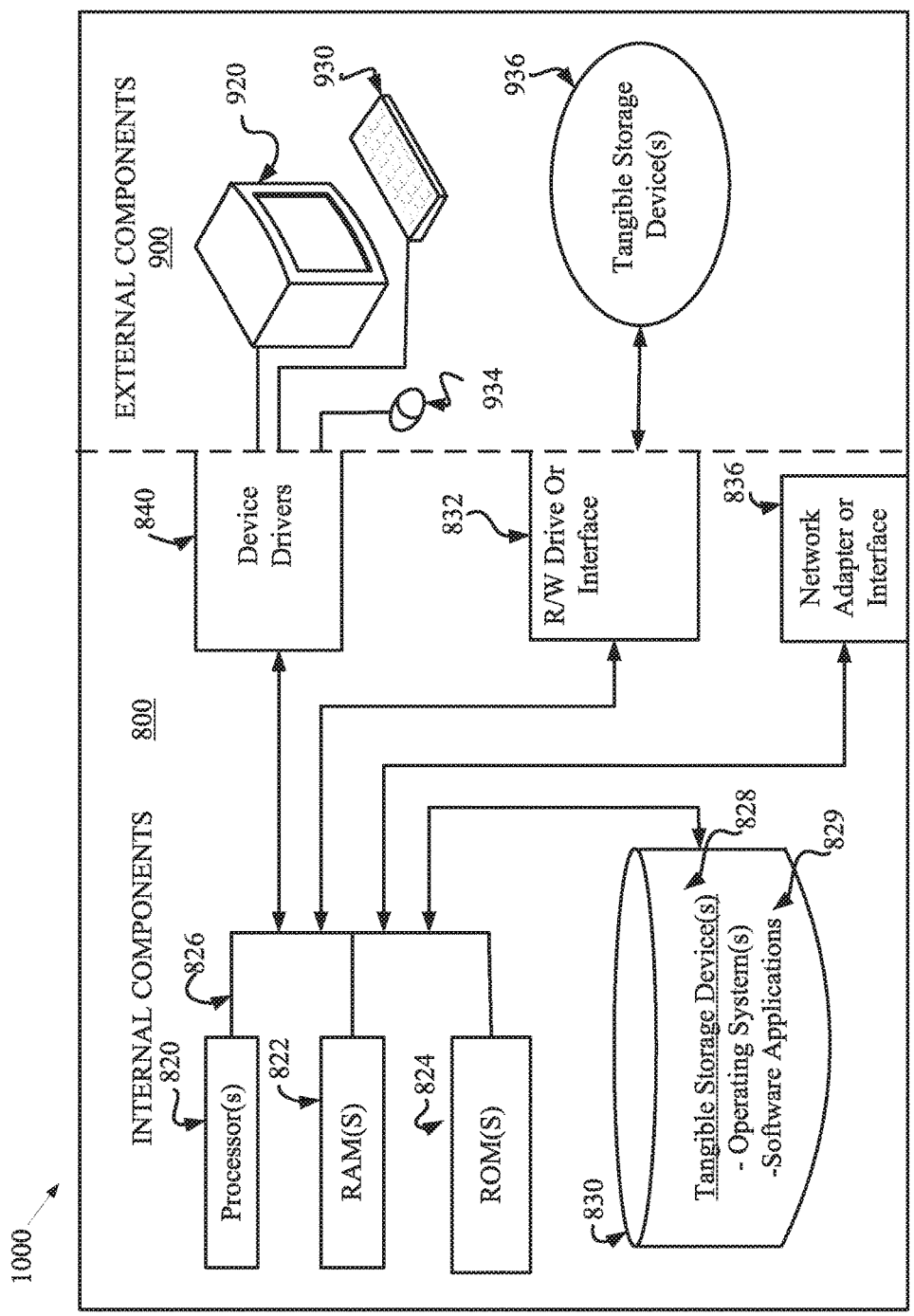
FIG. 5 is a schematic block diagram of a computer system, in accordance with an embodiment of the present disclosure.

Referring now to FIG. 5, a computing device 1000 may include respective sets of internal components 800 and external components 900. Each of the sets of internal components 800 includes one or more processors 820; one or more computer-readable RAMs 822; one or more computer-readable ROMs 824 on one or more buses 826; one or more operating systems 828; one or more software applications 829 (e.g., device driver modules) executing the method 400; and one or more computer-readable tangible storage devices 830. The one or more operating systems 828 and device driver modules are stored on one or more of the respective computer-readable tangible storage devices 830 for execution by one or more of the respective processors 820 via one or more of the respective RAMs 822 (which typically include cache memory). In the embodiment illustrated in FIG. 5, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800 also includes a R/W drive or interface 832 to read from and write to one or more computer-readable tangible storage devices 936 such as a thin provisioning storage device, CD-ROM, DVD, SSD, memory stick, magnetic tape, magnetic disk, optical disk or semiconductor storage device. The R/W drive or interface 832 may be used to load the device driver 840 firmware, software, or microcode to tangible storage device 936 to facilitate communication with components of computing device 1000.

Each set of internal components 800 may also include network adapters (or switch port cards) or interfaces 836 such as a TCP/IP adapter cards, wireless WI-FI interface cards, or 3G or 4G wireless interface cards or other wired or wireless communication links. The operating system 828 that is associated with computing device 1000, can be downloaded to computing device 1000 from an external computer (e.g., server) via a network (for example, the Internet, a local area network or wide area network) and respective network adapters or interfaces 836. From the network adapters (or switch port adapters) or interfaces 836 and operating system 828 associated with computing device 1000 are loaded into the respective hard drive 830 and network adapter 836. The network may comprise copper wires, optical fibers, wireless transmission, routers, firewalls, switches, gateway computers and/or edge servers.

Each of the sets of external components 900 can include a computer display monitor 920, a keyboard 930, and a computer mouse 934. External components 900 can also include touch screens, virtual keyboards, touch pads, pointing devices, and other human interface devices. Each of the sets of internal components 800 also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Figure 6:
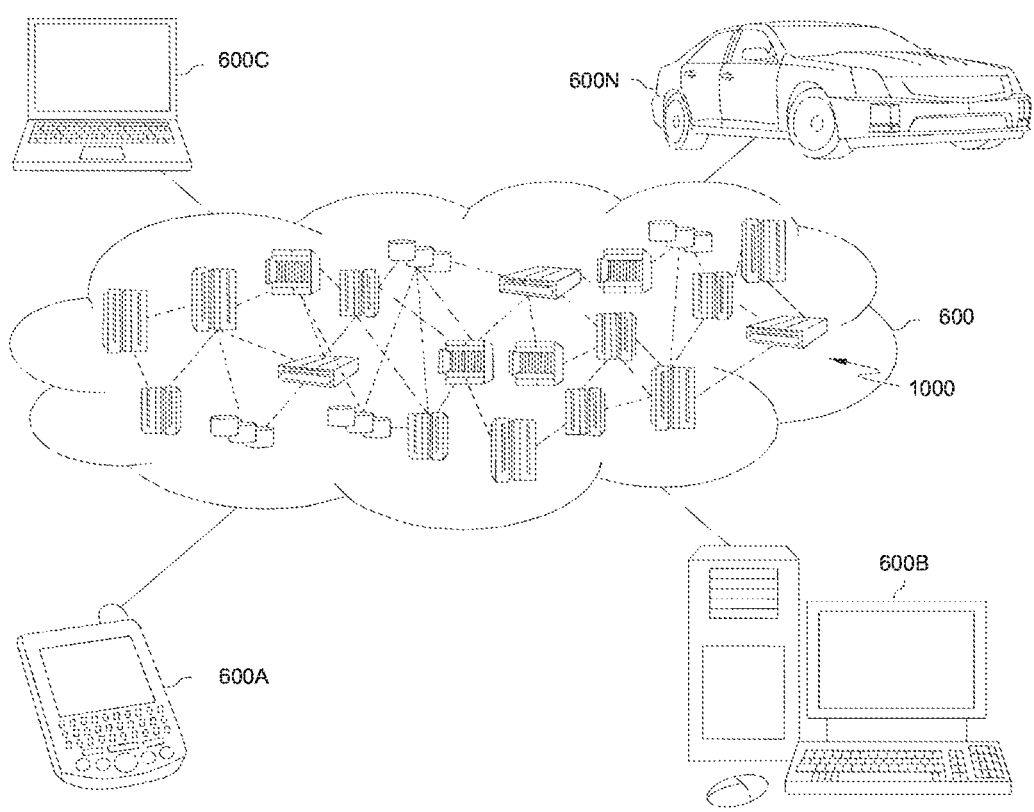
FIG. 6 is a block diagram of an illustrative cloud computing environment, in accordance with an embodiment of the present disclosure.

Referring now to FIG. 6, an illustrative cloud computing environment 600 is depicted. As shown, the cloud computing environment 600 comprises one or more cloud computing nodes, each of which may be a system 1000 with which local computing devices used by cloud consumers, such as, for example, a personal digital assistant (PDA) or a cellular telephone 600A, a desktop computer 600B, a laptop computer 600C, and/or an automobile computer system 600N, may communicate. The nodes 1000 may communicate with one another. They may be grouped (not shown) physically or virtually, in one or more networks, such as Private, Community, Public, or Hybrid clouds as described hereinabove, or a combination thereof. This allows the cloud computing environment 600 to offer infrastructure, platforms and/or software as services for which a cloud consumer does not need to maintain resources on a local computing device. It is understood that the types of computing devices 600A-N shown in FIG. 6 are intended to be illustrative only and that the computing nodes 1000 and the cloud computing environment 600 can communicate with any type of computerized device over any type of network and/or network addressable connection (e.g., using a web browser).

Figure 7:
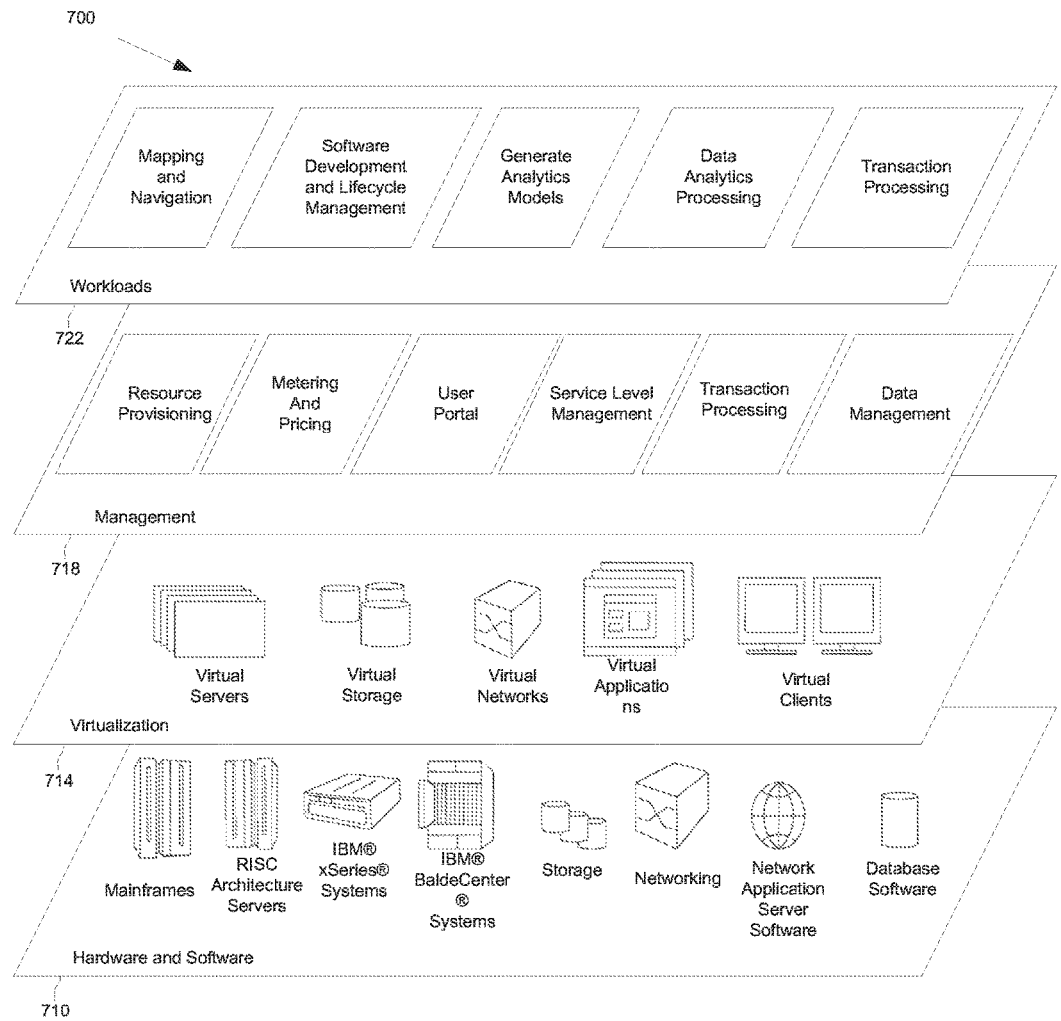
FIG. 7 is a block diagram of functional layers of the illustrative cloud computing environment of FIG. 6, in accordance with an embodiment of the present disclosure.

Referring now to FIG. 7, a set of functional abstraction layers provided by the cloud computing environment 700 (FIG. 6) is shown. It should be understood in advance that the components, layers, and functions shown in FIG. 7 are intended to be illustrative only and embodiments of the invention are not limited thereto. As depicted, the following layers and corresponding functions are provided.

The hardware and software layer 710 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

The virtualization layer 714 provides an abstraction layer from which the following examples of virtual entities may be provided: virtual servers; virtual storage; virtual networks, including virtual private networks; virtual applications and operating systems; and virtual clients.

In one example, the management layer 718 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

The workloads layer 722 provides examples of functionality for which the cloud computing environment may be utilized. Examples of workloads and functions which may be provided from this layer include: mapping and navigation; software development and lifecycle management; virtual classroom education delivery; data analytics processing; transaction processing; and an analytics modeling component, such as that provided for by embodiments of the present disclosure described in FIGS. 1-4B.

While the present invention is particularly shown and described with respect to preferred embodiments thereof, it will be understood by those skilled in the art that changes in forms and details may be made without departing from the spirit and scope of the present application. It is therefore intended that the present invention not be limited to the exact forms and details described and illustrated herein, but falls within the scope of the appended claims.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While steps of the disclosed method and components of the disclosed systems and environments have been sequentially or serially identified using numbers and letters, such numbering or lettering is not an indication that such steps must be performed in the order recited, and is merely provided to facilitate clear referencing of the method's steps. Furthermore, steps of the method may be performed in parallel to perform their described functionality.

What is claimed is:

1. A computer implemented method for generating an analytics model, the method comprising:
receiving a data set having a defined first set of features;
defining a second set of features based on an application of a set of domain knowledge data to the first set of features;
generating a features hierarchy based on relationships between features of the first and second sets of features; and
generating an analytics model based on a selection of features from the features hierarchy, wherein the analytics model includes features from the first and second sets of features while maintaining a defined accuracy value.

2. The method of claim 1, further comprising:
defining a third set of features based on any one or more of an aggregation of features of the first set of features and an aggregation of features of the second set of features; and
generating the features hierarchy based on relationships between features of the first, second and third sets of features.

3. The method of claim 1, wherein generating an analytics model further comprises:
generating the analytics model heuristically, whereby the analytics model is selected from a set of analytics models generated based on different features combinations of the features hierarchy.

4. The method of claim 1, further comprising:
determining an impact measure for each feature in the analytics model;
comparing the impact measure of each feature in the analytics model to the impact measure of at least one other feature in the analytics model; and
replacing each feature in the analytics model with the at least one other feature in the analytics model upon the at least one other feature having a preferred impact.

5. The method of claim 1, wherein the defined accuracy level is defined by a user.

6. The method of claim 1, wherein the set of domain knowledge data is defined by a user.

7. The method of claim 1, wherein the analytics model is a classification model including any one of a decision tree model, a Support Vector Machine (SVM) model, and a logistic regression model.

8. A computer system for generating an analytics model, comprising:
   a computer having a processor and a computer-readable storage device;
   a program embodied on the storage device for execution by the processor, the program having a plurality of program modules, the program modules including:
   a receiving module configured to receive a data set having a defined first set of features;
   a defining module configured to define a second set of features based on an application of a set of domain knowledge data to the first set of features;
   a first generating module configured to generate a features hierarchy based on relationships between features of the first and second sets of features; and
   a second generating module configured to generate an analytics model based on a selection of features from the features hierarchy, wherein the analytics model includes a highest number of features of the second set of features while maintaining a defined accuracy value.

9. The computer system of claim 8, further comprising:
   an additional defining module configured to define a third set of based on any one or more of an aggregation of features of the first set of features and an aggregation of features of the second set of features; and
   a third generating module configured to generate the features hierarchy based on relationships between features of the first, second and third sets of features.

10. The computer system of claim 8, wherein the second generating module further comprises:
    generating the analytics model heuristically, whereby the analytics model is selected from a set of analytics models generated based on different features combinations of the features hierarchy.

11. The computer system of claim 8, further comprising:
    a determining module configured to determine an impact measure for each feature in the analytics model;
    a comparing module configured to compare the impact measure of each feature in the analytics model to the impact measure of at least one other feature in the analytics model; and
    a replacing module configured to replace each feature in the analytics model with the at least one other feature in the analytics model upon the at least one other feature having a preferred impact.

12. The computer system of claim 8, wherein the defined accuracy level is defined by a user.

13. The computer system of claim 8, wherein the set of domain knowledge data is defined by a user.

14. The computer system of claim 8, wherein the analytics model is a classification model including any one of a decision tree model, a Support Vector Machine (SVM) model, and a logistic regression model.

15. A computer program product for generating an analytics model, comprising a tangible storage device having program code embodied therewith, the program code executable by a processor of a computer to perform a method comprising:
    receiving a data set by the processor, the data set having a defined first set of features;
    defining a second set of features, by the processor, based on an application of a set of domain knowledge data to the first set of features;
    generating a features hierarchy, by the processor, based on relationships between features of the first and second sets of features; and
    generating an analytics model, by the processor, based on a selection of features from the features hierarchy, wherein the analytics model includes a highest number of features of the second set of features while maintaining a defined accuracy value.

16. The computer program product of claim 15, further comprising:
    defining a third set of features, by the processor, based on any one or more of an aggregation of features of the first set of features and an aggregation of features of the second set of features; and
    generating the features hierarchy, by the processor, based on relationships between features of the first, second and third sets of features.

17. The computer program product of claim 15, wherein generating an analytics model further comprises:
    generating the analytics model heuristically, by the processor, whereby the analytics model is selected from a set of analytics models generated based on different features combinations of the features hierarchy.

18. The method of claim 15, further comprising:
    determining an impact measure, by the processor, for each feature in the analytics model;
    comparing the impact measure of each feature in the analytics model, by the processor, to the impact measure of at least one other feature in the analytics model; and
    replacing each feature in the analytics model, by the processor, with the at least one other feature in the analytics model upon the at least one other feature having a preferred impact.

19. The computer program product of claim 15, wherein the defined accuracy level is defined by a user.

20. The computer program product of claim 15, wherein the set of domain knowledge data is defined by a user.

* * * * *